(12) United States Patent
Cloutier et al.

(10) Patent No.: US 9,615,777 B2
(45) Date of Patent: Apr. 11, 2017

(54) SYSTEM AND METHOD FOR MONITORING OF ACTIVITY AND FALL

(75) Inventors: Christian Cloutier, St. Elzear (CA); Régis Fortin, Laval (CA)

(73) Assignee: Christian Cloutier, St-Elzear (CA)

(*) Notice: Subject to any disclaimer, the term of this patent is extended or adjusted under 35 U.S.C. 154(b) by 2148 days.

(21) Appl. No.: 11/297,368

(22) Filed: Dec. 9, 2005

(65) Prior Publication Data
US 2006/0139166 A1    Jun. 29, 2006

(30) Foreign Application Priority Data
Dec. 9, 2004  (CA) .................................... 2486949

(51) Int. Cl.
A61B 5/00   (2006.01)
A61B 5/11   (2006.01)
G08B 21/02  (2006.01)
G08B 21/04  (2006.01)

(52) U.S. Cl.
CPC .......... *A61B 5/1117* (2013.01); *A61B 5/0002* (2013.01); *A61B 5/1118* (2013.01); *A61B 5/4818* (2013.01); *G08B 21/0288* (2013.01); *G08B 21/0415* (2013.01); *G08B 21/0446* (2013.01); *A61B 2562/0219* (2013.01)

(58) Field of Classification Search
CPC ....... A61B 5/1117; A61B 5/1118; A61B 5/11; A61B 5/1112; A61B 5/1114; A61B 5/1116; A61B 5/1124; A61B 5/1126; A61B 5/02055; A61B 5/0002; A61B 5/4818; A61B 2562/0219; G08B 21/043; G08B 21/0446; G08B 21/02; G08B 21/0288; G08B 21/0415

USPC ........................................ 600/587; 340/573.7
See application file for complete search history.

(56) References Cited

U.S. PATENT DOCUMENTS

| | | |
|---|---|---|
| 4,110,741 A | 8/1978 | Hubert et al. |
| 4,829,285 A | 5/1989 | Brand et al. |
| 4,858,622 A | 8/1989 | Osterweil |
| 5,008,654 A | 4/1991 | Callaway |
| 5,045,839 A | 9/1991 | Ellis et al. |
| 5,146,206 A | 9/1992 | Callaway |
| 5,317,305 A | 5/1994 | Campman |
| 5,398,019 A | 3/1995 | Barnett et al. |
| 5,402,107 A | 3/1995 | Rencavage |
| 5,515,858 A | 5/1996 | Myllymaki |
| 5,544,661 A | 8/1996 | Davis et al. |
| 5,670,944 A | 9/1997 | Myllymaki |
| 5,682,882 A | 11/1997 | Lieberman |
| 5,751,214 A | 5/1998 | Cowley et al. |

(Continued)

FOREIGN PATENT DOCUMENTS

| | | |
|---|---|---|
| CA | 2275959 | 7/1998 |
| CA | 2399182 | 8/2001 |

(Continued)

*Primary Examiner* — Max Hindenburg
(74) *Attorney, Agent, or Firm* — Gwendoline Bruneau

(57) ABSTRACT

A system for monitoring activity of at least one subject in an environment, comprising at least one sensing assembly, detecting parameters in the environment; and a server communicating with at least one of: i) the subject and ii) the sensing assembly; the at least one sensing assembly comprising at least a first sensor connected to the region of the back of the neck of the subject, the first sensor unit comprising at least one accelerometer.

22 Claims, 9 Drawing Sheets

(56) References Cited

U.S. PATENT DOCUMENTS

| | | | |
|---|---|---|---|
| 5,774,055 A | 6/1998 | Pomerantz | |
| 5,853,005 A | 12/1998 | Scanlon | |
| 5,914,837 A * | 6/1999 | Edwards et al. | 360/265.6 |
| 5,919,149 A | 7/1999 | Allum | |
| 5,955,667 A | 9/1999 | Fyfe | |
| 5,963,891 A | 10/1999 | Walker et al. | |
| 6,048,324 A | 4/2000 | Socci et al. | |
| 6,102,856 A | 8/2000 | Groff et al. | |
| 6,148,280 A | 11/2000 | Kramer | |
| 6,160,478 A | 12/2000 | Jacobsen et al. | |
| 6,166,644 A | 12/2000 | Stroda | |
| 6,198,394 B1 * | 3/2001 | Jacobsen et al. | 340/539.12 |
| 6,201,476 B1 | 3/2001 | Depeursinge et al. | |
| 6,208,251 B1 | 3/2001 | Cadet et al. | |
| 6,239,704 B1 | 5/2001 | Olson | |
| 6,265,978 B1 | 7/2001 | Atlas | |
| 6,307,481 B1 | 10/2001 | Lehrman et al. | |
| 6,433,690 B2 | 8/2002 | Petelenz et al. | |
| 6,501,386 B2 | 12/2002 | Lehrman et al. | |
| 6,567,485 B1 | 5/2003 | Venier | |
| 6,570,503 B1 | 5/2003 | Ulert et al. | |
| 6,572,560 B1 | 6/2003 | Watrous et al. | |
| 6,582,380 B2 | 6/2003 | Kazlausky et al. | |
| 6,611,783 B2 | 8/2003 | Kelly, Jr. et al. | |
| 6,661,347 B2 | 12/2003 | Lehrman et al. | |
| 6,703,939 B2 | 3/2004 | Lehrman et al. | |
| 6,774,795 B2 | 8/2004 | Eshelman et al. | |
| 7,150,048 B2 * | 12/2006 | Buckman | 340/573.1 |
| 2001/0004234 A1 | 6/2001 | Petelenz et al. | |
| 2001/0021814 A1 | 9/2001 | Schomburg | |
| 2001/0032059 A1 | 10/2001 | Kelly et al. | |
| 2001/0048368 A1 | 12/2001 | Lehrman et al. | |
| 2002/0008630 A1 | 1/2002 | Lehrman et al. | |
| 2002/0116080 A1 * | 8/2002 | Birnbach et al. | 700/66 |
| 2002/0118121 A1 | 8/2002 | Lehrman et al. | |
| 2003/0018430 A1 | 1/2003 | Ladetto et al. | |
| 2003/0093003 A1 | 5/2003 | Watrous et al. | |
| 2003/0139692 A1 | 7/2003 | Barrey et al. | |
| 2003/0153836 A1 | 8/2003 | Gagnadre et al. | |
| 2004/0010390 A1 | 1/2004 | Kelly, Jr. et al. | |
| 2004/0015103 A1 | 1/2004 | Aminian et al. | |
| 2004/0021569 A1 | 2/2004 | Lepkofker et al. | |
| 2005/0059902 A1 * | 3/2005 | Itagaki | 600/587 |

FOREIGN PATENT DOCUMENTS

| | | | |
|---|---|---|---|
| EP | 1 128 349 | 8/2001 | |
| EP | 1 195 139 | 4/2002 | |
| WO | WO 00/69517 | 11/2000 | |
| WO | WO 03/065891 | 8/2003 | |
| WO | WO 2004012592 A1 * | 2/2004 | A61B 5/00 |

* cited by examiner

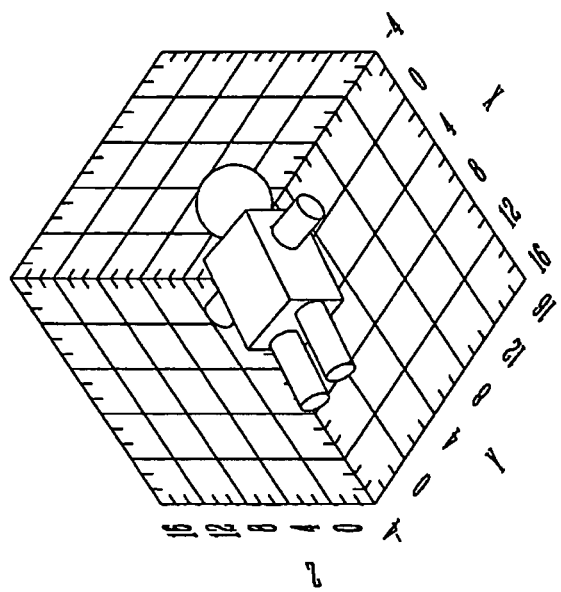
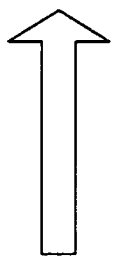
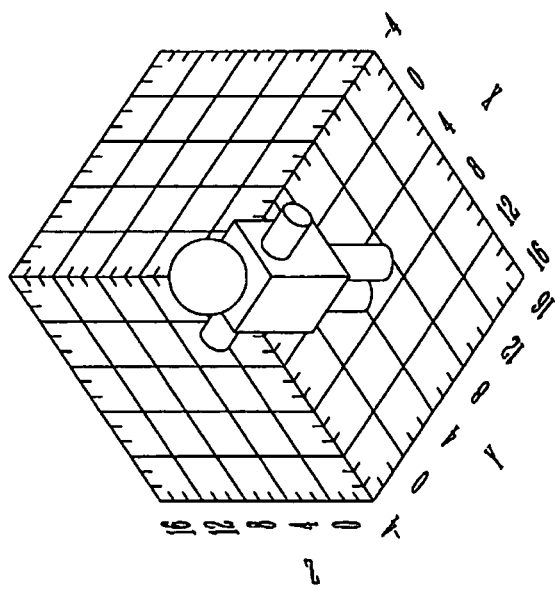
Fig-8

SYSTEM AND METHOD FOR MONITORING OF ACTIVITY AND FALL

CROSS REFERENCE TO RELATED APPLICATIONS

This application claims priority on Canadian application no. CA 2,486,949, filed on Dec. 9, 2004. All documents above are herein incorporated by reference.

FIELD OF THE INVENTION

The present invention relates to monitoring of a subject. More specifically, the present invention is concerned with a system and a method for monitoring of activity and fall of a subject.

SUMMARY OF THE INVENTION

More specifically, there is provided a system for monitoring activity of at least one subject in an environment, comprising at least one sensing assembly, detecting parameters in the environment; and a server communicating with at least one of: i) the subject and ii) the at least one sensing assembly; wherein the at least one sensing assembly comprises at least a first sensor connected to the region of the back of the neck of the subject, the first sensor unit comprising at least one accelerometer.

There is further provided a system for monitoring activity of a subject in an environment, comprising at least one sensing assembly, detecting parameters of the given environment; and a server communicating with at least one of: i) the subject and ii) the at least one sensing assembly; wherein the at least one sensing assembly comprises at least a first sensor unit at the back of the neck of the subject.

There is further provided a method for monitoring activity of a subject in an environment, comprising providing at least one sensing assembly in the environment of the subject; providing a server communicating with at least one of: i) the subject and ii) the at least one sensing assembly; generating property vectors from data collected by the at least one sensing assembly; characterizing activity of the subject from the property vectors; and having a result of said characterizing step accessible to the server.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

In the appended drawings:

FIG. 8 is a diagram of positioning obtained by a method according to the present invention;

DESCRIPTION OF EMBODIMENTS OF THE INVENTION

Figure 1:
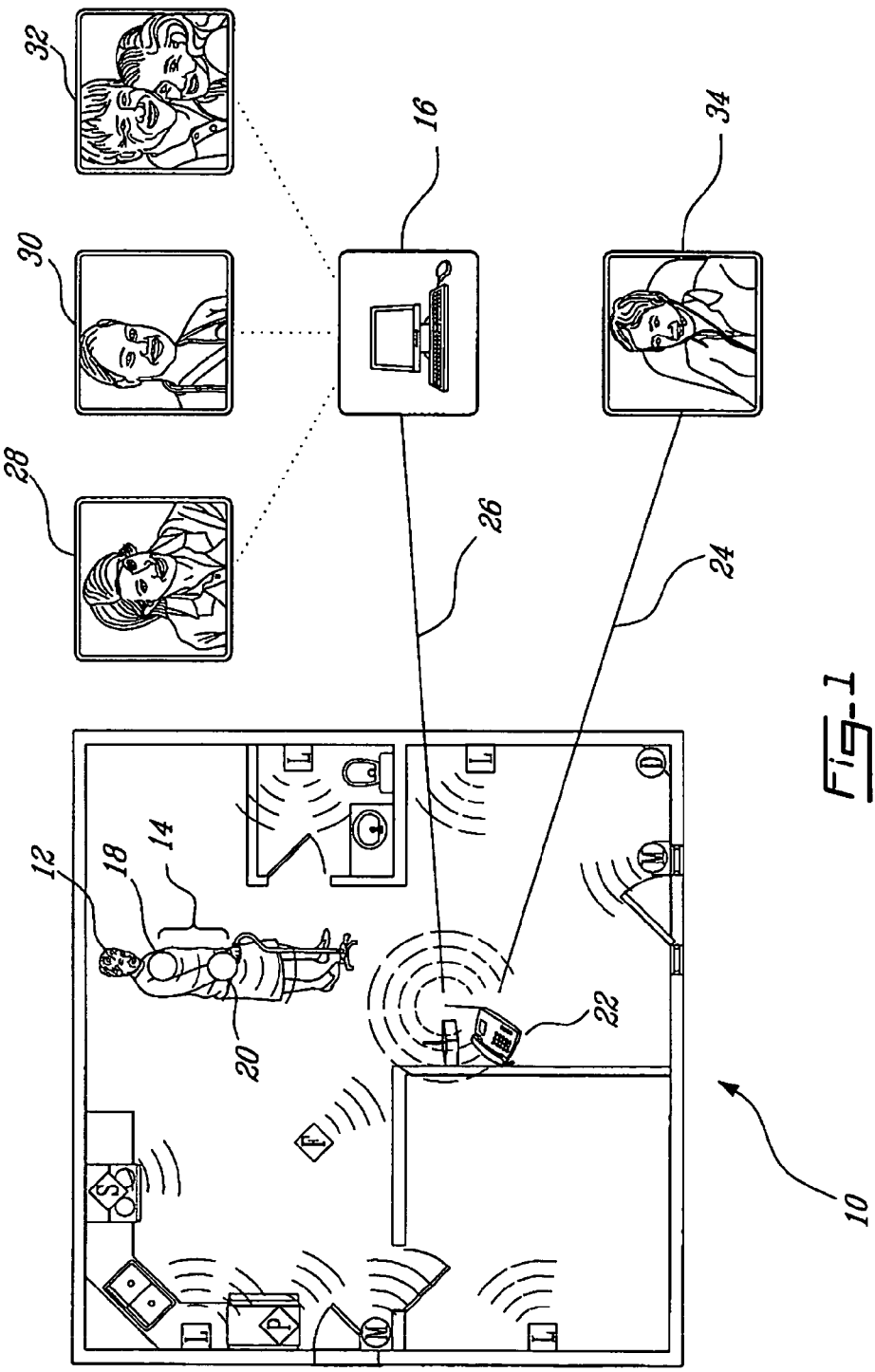
FIG. 1 is a diagram of a first embodiment of a system according to the present invention.

A system as illustrated in FIG. 1 comprises a sensing assembly 14 and a server 16, a subject to be monitored 12 being in its environment 10.

The sensing assembly 14 illustrated in the embodiment of FIG. 1 comprises a first sensor unit 18, located in the region of the neck of the subject 12, for example integrated in a neck assembly worn by the subject 12, and a second sensor unit 20 located in the region of the diaphragm, or/and the fist and/or of the leg of the subject 12, for example in a wrist band.

The sensor units include at least one 2- or 3-axes accelerometers. They may further comprise a gyroscope. The respective number, combination and location of the different sensors depend on target monitoring data, as will be explained hereinbelow.

For example, the first sensor unit 18 may comprise a high G accelerometer and a low G accelerometer, while the second unit sensor 20 comprises a low G accelerometer, both optionally further comprising a gyroscope.

Alternatively, the sensor unit 18, located at the base of the neck of the subject 12, integrated in a neck assembly that the subject 12 wears, may comprise a three-axes high G sensor and a gyroscope. The sensor unit 20, worn as a bracelet, comprises a low G accelerometer and a gyroscope. The sensing assembly 14 communicates with a base 22, located in the environment 10 of the subject 12. This base 22 is connected by a phone link 24 and by Internet 26 to a server 16 for information exchange. Access to the remote server 16 is controlled and allows target persons, such as a physician 28, employees of a health center 30, members of the family 32 of a human subject 12 for example, as well as a call center 34 to monitor data and profiles corresponding to the subject 12 from a distance. The remote server 16 is also used as an interface for sending messages and instructions to the different parts of the system.

The system automatically detects falls and critical activity levels of the subject 12 and is able to emit a request for intervention or alarm, as will be further described hereinbelow.

The base 22 may support a remotely modifiable and programmable reminder function useful for assisting subjects with a cognitive deficiency, whereby remote-intervention functions are allowed. The base 22 may also comprise means for processing data and alarms received from the sensing assembly 14, as well as means for bi-directional voice communication. It may further support a mobile unit of the wireless type offering similar features as just described and optionally integrating GPS localization means allowing monitoring the subject 12 outdoors for example.

Figure 2:
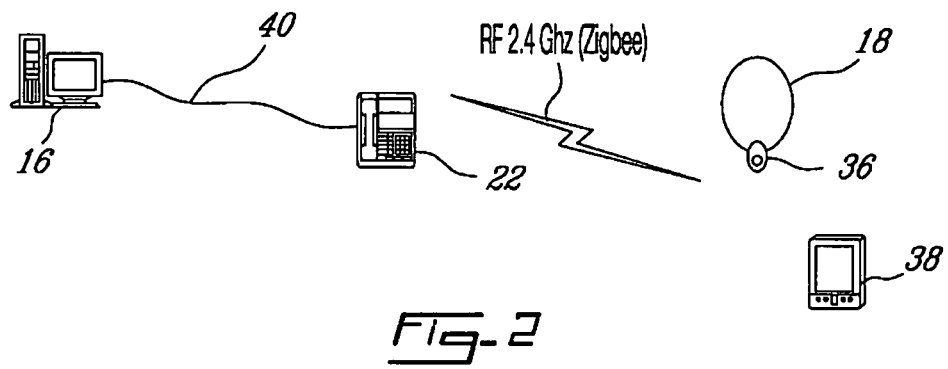
FIG. 2 is a diagram of a second embodiment of a system according to the present invention.

In the embodiment illustrated in FIG. 2, the sensor assembly 14 consists of a sensor unit 18 comprising a 3-axes high G sensor and a gyroscope, integrated in a neck assembly worn by the subject 12. The neck assembly comprises RF communication means to the base unit 22, and a device for asking help 36. The base 22 is a hands-free unit allowing wireless communication, through a 2.4 GHz RF link of a ZIGBEE® network for example, to the neck assembly and optional detectors 38. The base 22 includes a help button and a reset button. The base 22 is linked to a remote server 16 by standard telephone network 40.

Figure 3:
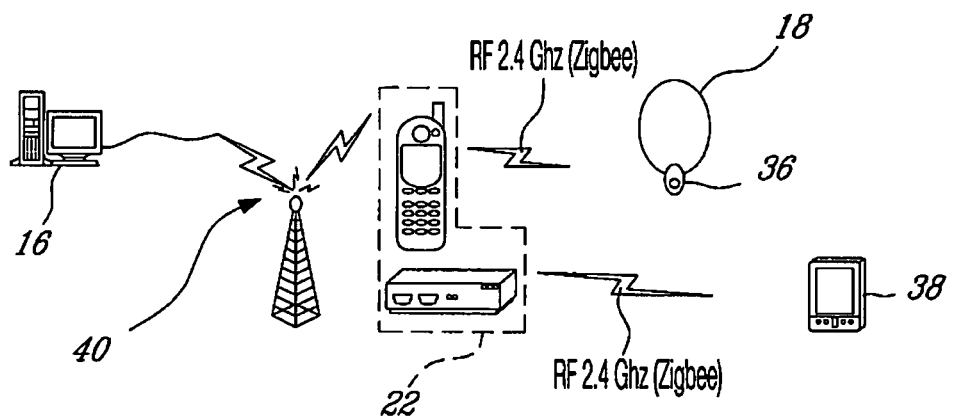
FIG. 3 is a diagram of a third embodiment of a system according to the present invention.

In the embodiment illustrated in FIG. 3, the base 22 is a free-hands phone allowing wireless communication with the sensor unit 18 and optional detectors 38 on the one hand, and to a remote server 16 via a cellular network 40 on the second hand.

As exemplified in FIG. 1, optional detectors 38 may include for example three-dimensional locaters and interphones (L), motion sensors (M) and presence detectors (D), pillbox sensor (P), smoke detectors (F) and household-appliance detectors (S).

Figure 4:
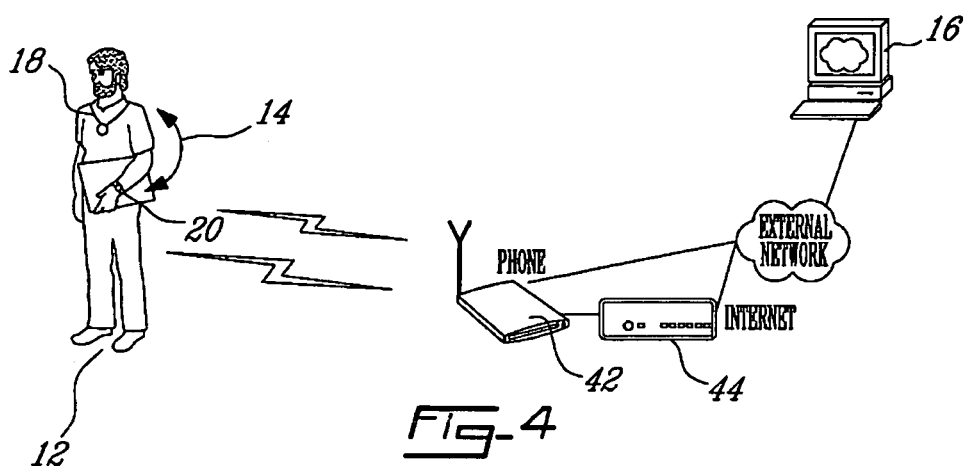
FIG. 4 is a diagram of a fourth embodiment of a system according to the present invention.

In the embodiment illustrated in FIG. 4, the subject 12 wears a first sensor unit 18 as a neck assembly and a second sensor unit 20 as a wristband. Both sensor units are connected by a unidirectional low frequency low power RF communication link. The sensor unit 20 is connected to a 900 MHz bidirectional receiver 42. The receiver 42, connected to a modem cable or DSL 44, sends data in case of alarm to, or transfer data upon request of, a remote server 16, using an external network accessed either by phone and/or by the Internet.

Figure 5:
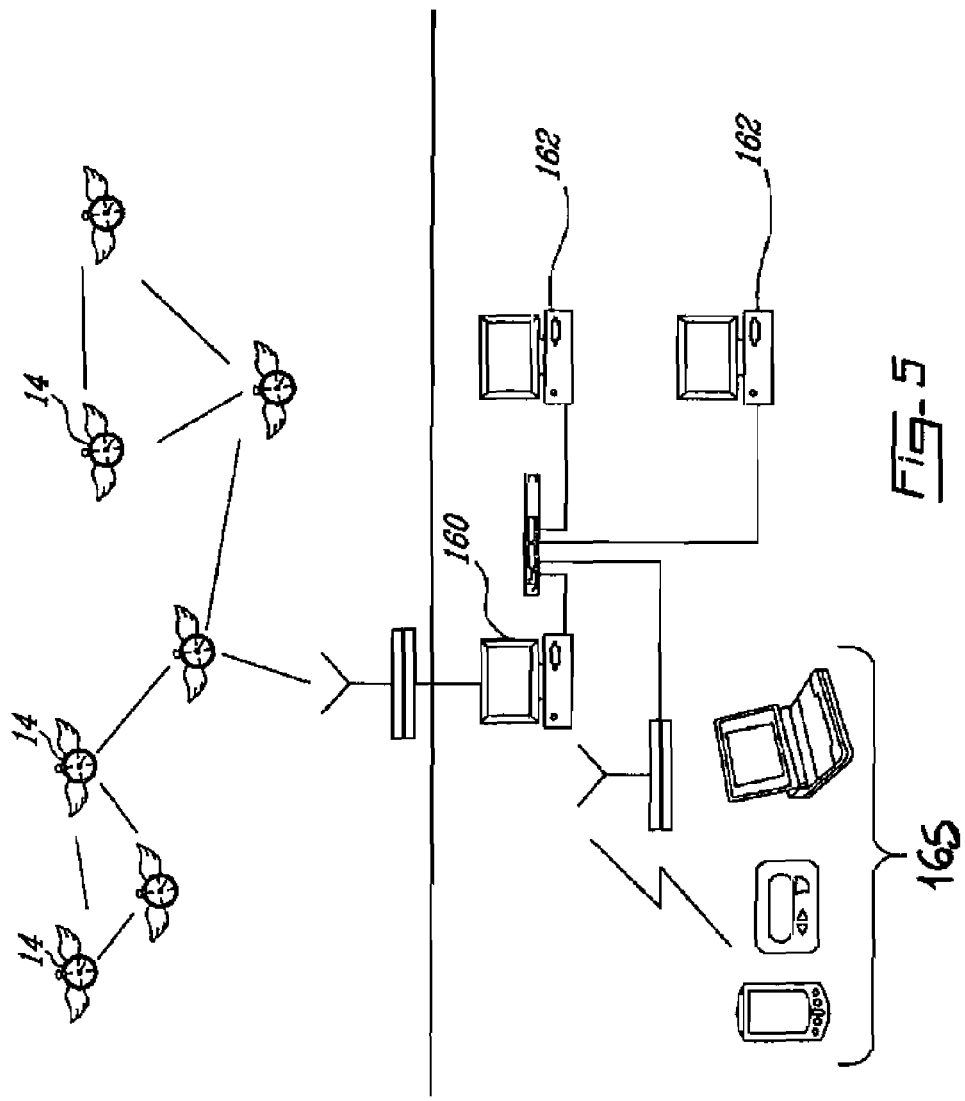
FIG. 5 is a diagram of a fifth embodiment of a system according to the present invention.

In the embodiment illustrated FIG. 5, a plurality of sensing assemblies 14 are arranged as a 900 MHz network of the a local network type for example, for monitoring a plurality of subjects, for example in a shelter for elderly in the case of human subjects, or a herd. The resulting network of sensing assemblies 14 is linked to a central server 160 connected to other servers 162 used for accessing information provided by the central server 160, and connected to mobile units 165 by a wireless network.

These systems allow collecting data related to the dynamics of the movements of least one subject to be monitored.

The sensor unit 18 in the upper part of the body of a person being monitored, or in the front part of an animal being monitored for example, typically comprises a high G accelerometer to detect fall of the subject. It may further comprise a low G accelerometer to follow the position of movements of the subject. The frequency, velocity and space orientation of movements of the upper trunk of the subject is used to yield movement levels, which can be graded from null to intense. These parameters may be processed using a variety of tools such as fuzzy logic, threshold parameters or a weighting mechanism for example.

For example, energy levels may be obtained as an average of the sum of the absolute values of acceleration along the three axes of the 3 axis accelerometer for example, corrected by an off set characterizing the sum of these accelerations at rest (since accelerometers measure not only the energy involved during a movement of the person, but also the gravitational force the person is submitted to), over a number of measurements per second. This off set is to be taken into account, considering that acceleration generated by a moving person is within the range between about −2G and +2G on a one second cycle basis, while the gravitational force is generally about 9.8 m/s/s, i.e. the signal corresponding to the gravitational force may be stronger than those corresponding to the person's movements.

In a particular embodiment, the energy level (NE) are thus obtained as follows: the OG (offset) value of each accelerometer is measured acceleration along the three axes thereof, by placing each axis in perfect alignment with the direction of the gravitational force, yielding the values $X_{offset}$, $Y_{offset}$ and $Z_{offset}$. In practice, the offset values may be set during the fabrication stage of the accelerometer, for example by making the OG value correspond to an octet value of 128 (the octet 0 being related to −5G, and the octet 255 corresponding to +5G). The energy level NE is calculated as the average over 142 vectorials modules $NE_i$, during a period of one second, 142 being the number of sample by second samples, wherein each vectorial module $NE_i$ is the square root of the sum of the squared corrected values axes. A new NE value is generated every second and stored. This indicator NE allows quantifying the intensity of movements thus provides energy levels over periods of 1, 5, 30 minutes or more.

A second indicator NM, may be used to quantify the movement levels, describing in particular movements of low amplitude. A detector having a maximum and a minimum on each axis of the accelerometer is used, on 1-second periods of time. By subtracting this minimum to that maximum, the offset is obtained. The NM value is generated and stored simultaneously with the NE.

A gain KM for the movement level NM and a gain Ke for the energy level NE may be defined and used to generate an indicator of movement level.

A third indicator, referred to as INC, may be used to identify a fall event, as detected by an impact sensor, by comparison to an adjustable threshold. The impact sensor measures a gradient and amplitude of shock waves related to a fall, typically characterized by 10 waves over 0.25 seconds. The fall indicator INC may be defined as the sum of absolute values of amplitudes measured during an event. Typically, an INC of 25% corresponds to low amplitude impacts, while severe falls are characterized by INC values of 100% and more.

Such data may further be used to determine sub-levels of sleeping activity, including sleep phases and intensity, or levels of low-intensity activities such as rest or writing process.

The sensor assembly of the present invention allows identifying critical levels of activity, as defined according to a target population of subjects to be monitored, such as persons suffering from functional dependence for example. Critical levels may be set for a range of activities, including a total lack thereof such as in case of death, breathing rhythms and apnea, breathing in absence of minimal movement such as in case of coma or faintness, and hyperactivity.

A preliminary classification of the persons to be monitored according to their degree of physical sufficiency allows setting threshold and control parameters adapted individually to each of these persons and to yield data all the more representative of the state of each one of them.

Nycthemeral or circadian analysis may be used to obtain activity patterns of a subject for time monitoring and identification of abnormal or undesirable variations in time of the subject.

Activity of the subject may be qualitatively assessed, be it walking, feeding or sleeping for example, by analyzing the data collected by the sensing assembly of the system by processing based on neural networks in combination with fuzzy logics or logic threshold values, depending on the processing and memory capacity available.

As described hereinabove, the present system, using at least one sensing assembly comprising at least one a high G accelerometer, may be used for monitoring a fall of this subject and a low-G one for monitoring his-her activity level. Turning to FIGS. 6 to 10 of the appended drawings, embodiments of a method according to the present invention method will now be described.

Figure 6:
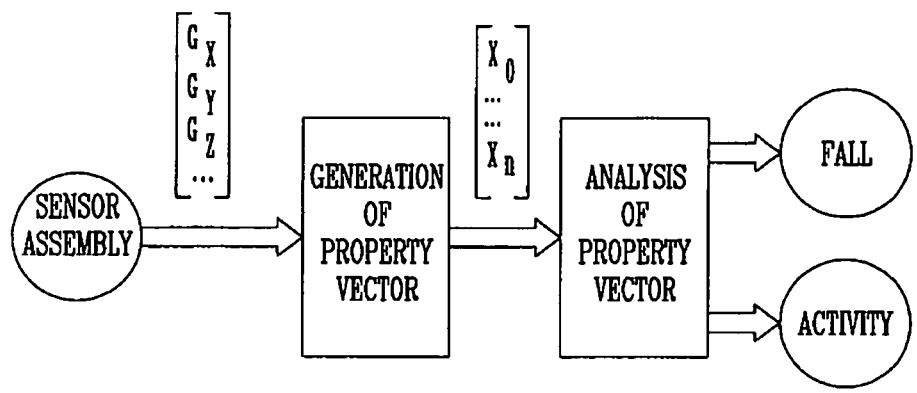
FIG. 6 a flowchart of an embodiment of a method according to the present invention.
Figure 7:
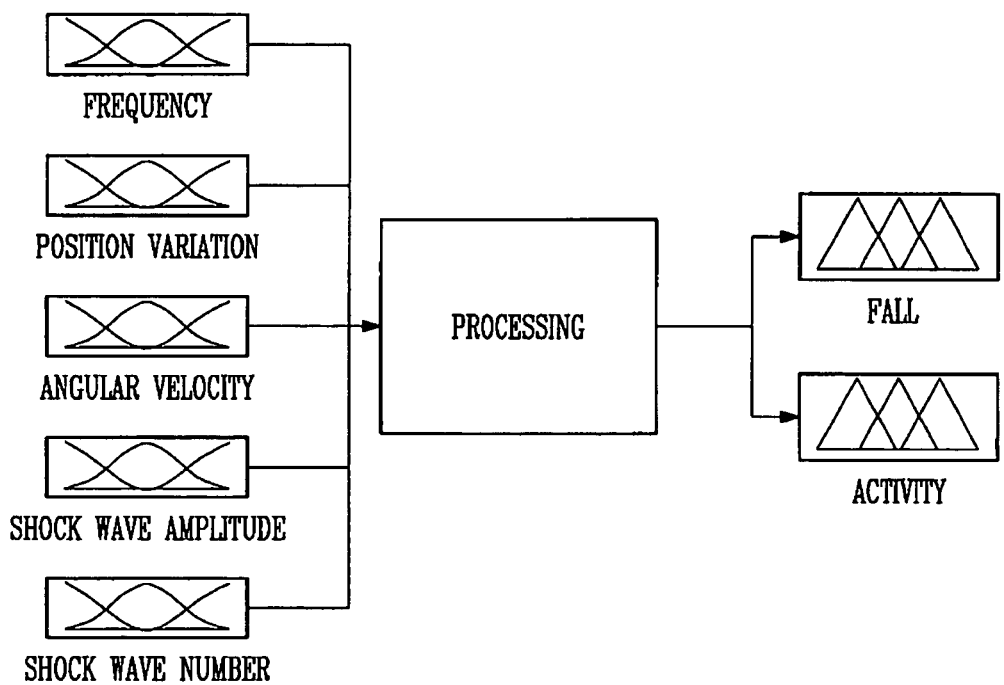
FIG. 7 is a flowchart of another embodiment of a method according to the present invention.

In FIG. 6, for example, the sensing assembly provides analog signals emitted by at least a 3-axes accelerometer and two gyroscopes. These signals are digitized by an analog-to-digital converter. The obtained data are placed in a memory stack storage used as a short-term memory, and which size defines the term in seconds. Low-level algorithms are applied to the data of the memory stack storage to extract data on the behavior and body posture of the subject being monitored, by generating a property vector from these data. Such property vector includes a number of parameters as follows (see FIG. 7):

frequency of the body movement, defining the activity of the monitored subject by the absence of activity, the rest, moderate and active awaken states;

trunk position variation: data collected by the accelerometer allow determining the space orientation of the accelerometer, which is related to the space orientation (x, y, z) of the monitored subject, through gravity and knowledge of the location of the accelerometer in relation to the body of the monitored subject (see FIG. 8);

height of the monitored subject along a z direction, which may be used to sort out actual fall events from false alarms by correlating this height with the position of the body (see FIG. 8);

angular velocity of the trunk of the monitored subject, which may be used to determine whether a trunk position variation results from a controlled movement or from an accidental movement;

shock wave amplitude, characterizing a fall event;

number of shock waves, which may be used to sort out actual fall events from false alarms.

As shown in FIG. 8, the position of the monitored subject includes his-her position along a vertical axis (noted z in the Figure), which allows assessing the height of an event taking place in a (x,y) plane, i.e. determining whether the monitored subject is lying on the floor, lying on top of a bed, seated, kneeling down, or standing. Measuring the position along the vertical axis may be achieved by RFID (radio frequency identification), ultrasound or using a camera for example.

The property vector is analyzed to determine whether the monitored subject has fallen and to yield indications on the type of activities the subject is involved in. Fuzzy logics analysis may for example be used to yield to output information, relating to fall and activity respectively.

Using a sensing assembly comprising a sensor unit in the upper part of the subject combining a high frequency-low accuracy (high G in the range of 100 G) accelerometer and a low frequency-high accuracy (low G in the range between 2 and 5 G) accelerometer, allows detecting events such as impact as well as body posture and fine movements.

Moreover, the locations of the sensor units of the sensing assembly relative to the monitored subject's body may be selected to combine a sensor unit at the wrist of the monitored subject with a sensor unit in the region of the base of the neck for example. The combination of these sensor units allows tracking the dynamics of the trunk of the monitored subject while allowing discarding non-pertinent interferences due to non-significant movements for example. Furthermore, this combination allows detecting a fall event while reducing false-alarms generation, since, for example in the case of a single wrist sensor unit, even a knock of the hand wearing the wrist sensor unit on a table for example would be detected as an impact.

Such a combination of the locations of the sensor units allows sorting events, by allowing a validation between impacts or movements usually of lower amplitude of the trunk of the monitored subject and impacts or movements usually of higher amplitude of the arm of the monitored subject. It further allows a qualitative assessment of events, by allowing for example to identify a movement of the arm alone as a protection movement.

The sensor unit in the region of the trunk of the monitored subject may be efficiently connected to the monitored subject without use of straps, since a neck assembly for example may be used, as described earlier hereinabove.

A gyroscope included in the sensor unit located at the base of the neck or trunk of the monitored subject allows measuring angular velocities, i.e. velocity of lateral movements (left to right and right to left) and back and forth movements of the trunk of the monitored subject. Moreover, data from such gyroscope are used to determine threshold values of angular velocities.

Figure 9:
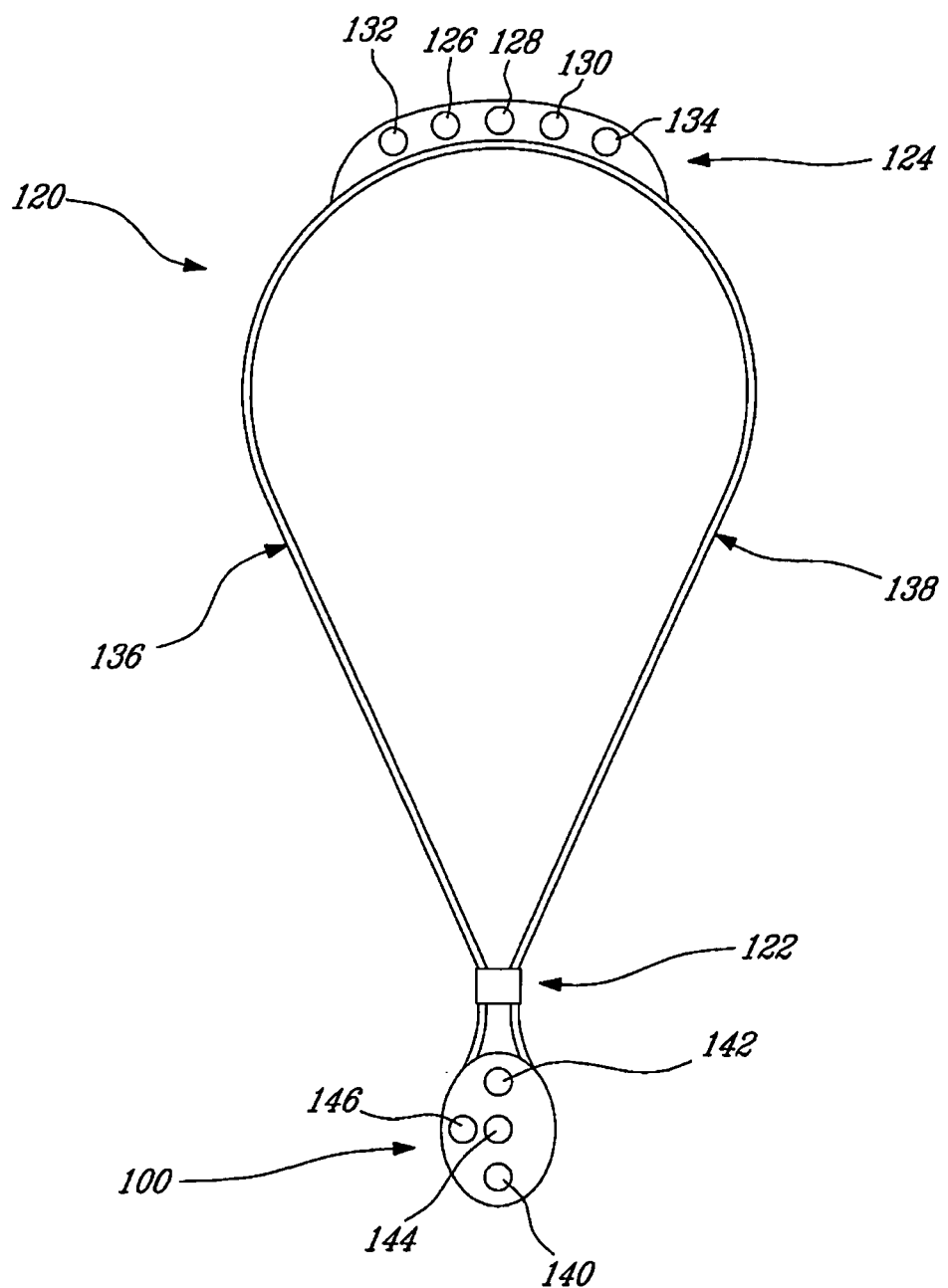
FIG. 9 illustrates an embodiment of a neck assembly according to the present invention.

FIG. 9 illustrates an embodiment of a neck assembly 120 of a bolo tie type for locating a sensor unit. A clip 122, besides allowing adjusting a length of the assembly 120 around the neck of the person to be monitored, acts as a balancing weight securing the assembly 120 in place as the monitored person moves. The region of the assembly 120 placed in the back of the neck comprises a flexible unit 124 housing sensors, including a 2-5 G accelerometer 128 and a 50 G accelerometer 126, and optionally a gyroscope 134, a thermistor 130, and an impedance detector 132 for monitoring wearing of the assembly. The assembly 120 comprises an RF antenna 138 and a link 136 between the flexible unit 124 and a pendant 100. The pendant 100 houses a microphone 140, a 3D positioning unit 142, a help summon button 144 and a battery 146.

Figure 10:
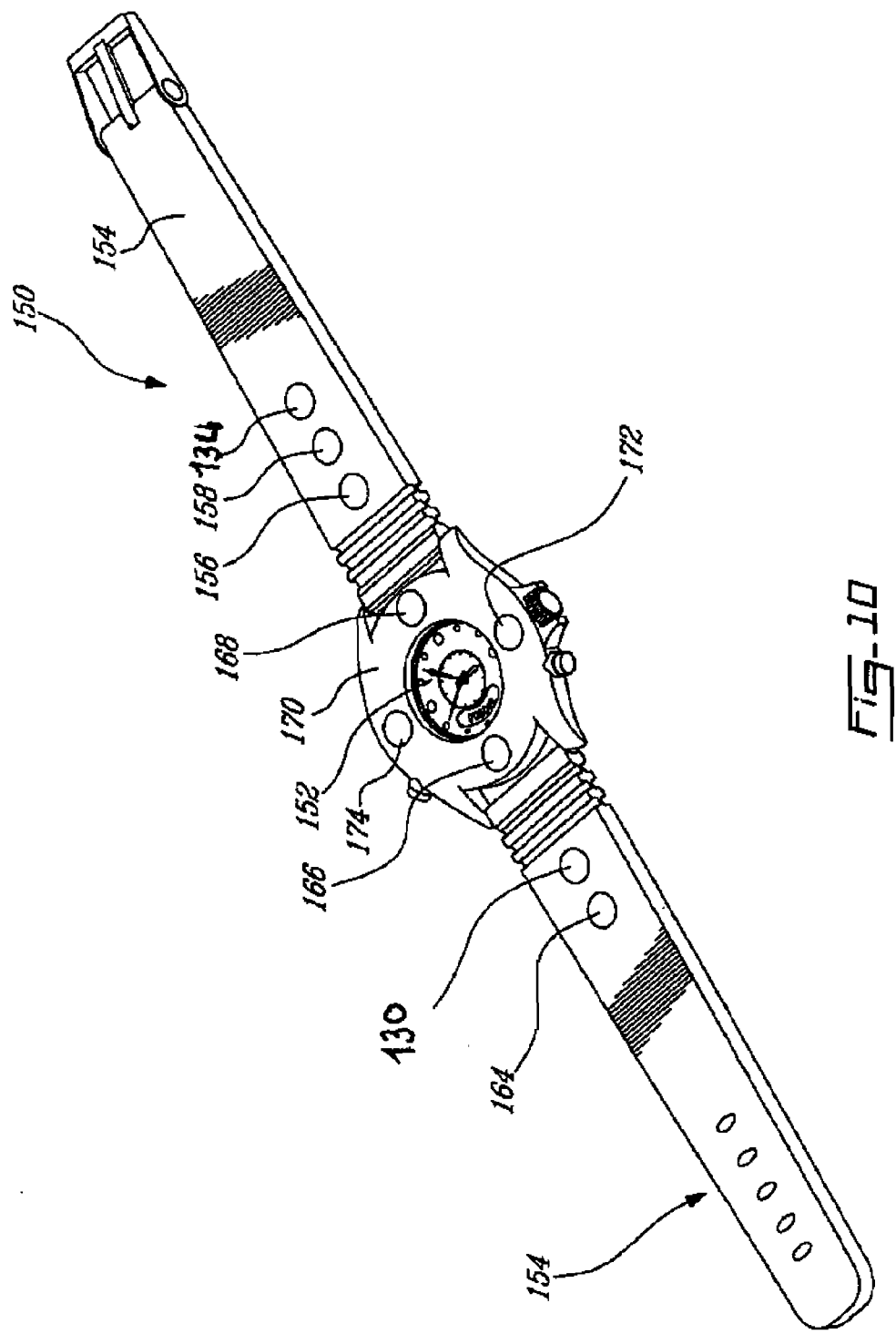
FIG. 10 illustrates an embodiment of a wrist assembly according to the present invention.

FIG. 10 illustrates an embodiment of a wrist assembly 150 of a wristwatch band type for locating a sensor unit. The bracelet part 154 integrates the sensors, including a 2-5 G accelerometer 156, a 50 G accelerometer 158, a gyroscope 134, a thermistor 130 and an impedance detector 164 for monitoring wearing of the assembly. The module 152 comprises a microphone 166, a 3D positioning unit 168, a help summon button 170, a battery 172 and a clock 174.

Data from a detector for monitoring wearing of the assembly (132, 164 in FIGS. 9 and 10 for example) may be integrated with data from the accelerometers and other sensors so as to further discriminate between events, between a fall of the monitored person and the monitored person merely dropping the neck assembly 120 or of the wrist assembly 150 on the floor for example.

Such system and method allows identification of critical activity levels, such as coma states, immobility over a period of time, breathing movements interruption, thereby allowing establishing a profile of daily nycthemeral activities of the monitored subject for example. Such profile may be used for detecting sudden variations, which may be significant of a decline in the monitored subject's well being, and provide information concerning the evolution of parameters of the profile of daily nycthemeral activities of the monitored subject, weighted according to the initial functional independence level of the monitored subject to permit assessment of functional independence variations.

Figure 12:
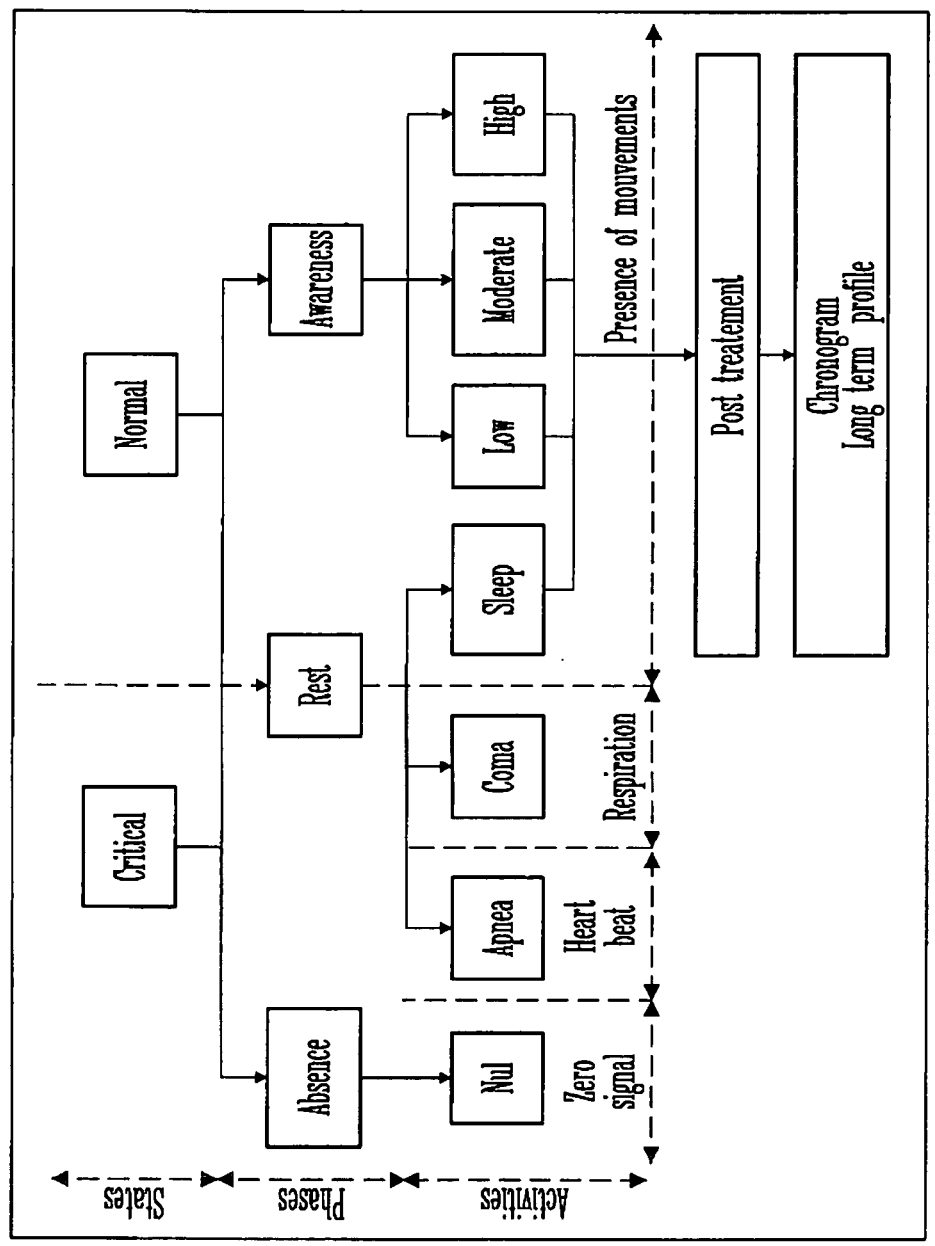
FIG. 12 is a diagram showing the results obtained by a method according to the present invention.

Acceleration, velocity and/or position signals sampled on at least one sensing assembly comprising a sensor unit located on the trunk, and, optionally, a sensor unit located on the wrist of the monitored subject, each sensing assembly comprising an accelerometer and optionally a gyroscope and/or a piezo-film, may be used to provide a representation for the behavior of the monitored subject through activity levels (see FIG. 12).

Figure 11:
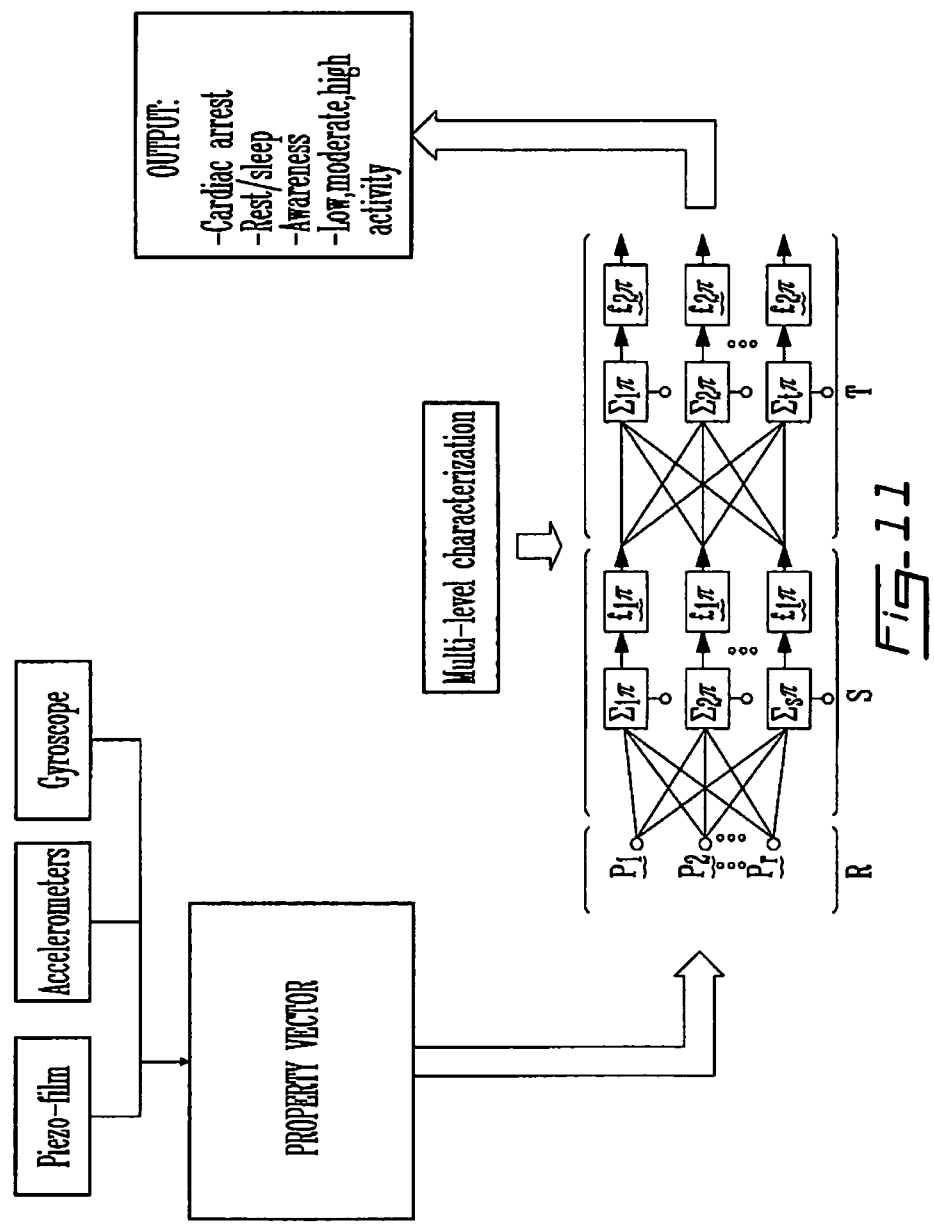
FIG. 11 is a flowchart of a further embodiment of a method according to the present invention.

The activity levels are characterized using indicators (such as NE, NM, INC discussed hereinabove for example) on the body posture of the monitored subject and of any change in her-his position in her-his environment, of the velocity and quantity of movements of each part of her-his body wearing a sensor unit, obtained from processing the acceleration, velocity and/or positional signals collected by the sensing assembly. As described hereinabove, these indicators or property vectors are analyzed to yield the state, phase of state and activities of the monitored subject, and the evolution thereof during a predetermined period of time (see FIG. 11).

As illustrated in FIG. 12, the state of the monitored subject may be assessed between a critical state corresponding to a problem or an activity level indicating a potentially deficient well being, and a normal state. In each case, an absence of movement as indicated by the absence of movement detection, may be interpreted as a defective system or as the death of the monitored subject, while slow heart beat, breathing movements and minimal body movements may be interpreted as representative of a rest phase of the monitored subject, and body or member movements, as characterized by their frequency, velocity and orientation, may be evidence of an awareness phase of the monitored subject. In each of these phases, different activity levels may then be assessed, from null in the phase of absence of detection), to apnea (heart beats are detected), coma (breathing is detected), and sleep (movements are detected) in the rest phase, and to low, moderate and high activity levels (movements are detected) in the awareness state.

The frequency analysis of signals collected at the base of the neck of the monitored subject yields a quantitative assessment of the movement of the monitored subject, including the variations of this quantity of movements during short periods of time.

The analysis of signals collected at the wrist of the monitored subject may be combined to yield a qualitative assessment of this movement by incorporating angular velocity measurements and positional measurement in space (x, y, z). The combined analysis of signals emitted in the region of the base of the neck and of signals emitted in the region of the wrist yield an accurate activity profile and efficient positioning along the vertical axis (z). This in turn results in a possible identification of the very room in which an event occurs (bathroom, kitchen, bedroom etc. . . . ) by cross-correlation, and therefore to an increasingly efficient monitoring system, since allowance levels may be predetermined individually for each room of the subject's habitat, considering for example that the subject detected lying on her-his bed in her-his-bedroom and sleeping is reasonably a normal event.

Therefore the present system and method allow monitoring a subject very precisely in relation to her-his individual functional independence level as well as his-her environment.

Although embodiments were illustrated given hereinabove in relation to a human, the present system and method may efficiently be applied for monitoring a range of subjects, including for example farm animals, domestic pets etc. . . .

Although the present invention has been described hereinabove by way of embodiments thereof, it may be modified, without departing from the nature and teachings of the subject invention as defined in the appended claims.

What is claimed is:

1. A system for monitoring activity of a subject and occurrence of a fall of the subject, said system comprising:
   a sensing unit configured for placement at the base of the back of the neck of the subject, said sensing unit being configured for a low G/high G acceleration sensing range; and
   a base configured to wirelessly communicate with said sensing unit;
   said sensing unit being configured to wirelessly transmit acceleration data measured by said sensing unit in the low G and in the high G acceleration range and correlated to the spine of the subject due to said placement at the base of the back of the neck of the subject;
   wherein said base is configured to receive said acceleration data measured by said sensing unit in the low G and in the high G acceleration range and sent by said sensing unit;
   said base being further configured to process the acceleration data in the low G and in the high G acceleration range into data reflecting a vectorial position of the spine of the subject due to said placement at the base of the back of the neck of the subject;
   said base being further configured to identify a fall of the subject based at least on said acceleration data measured by said sensing unit in the high G range and to determine levels of activity of the subject based at least on said acceleration data measured by said sensing unit in the low G range.

2. A system for monitoring activity of a subject and for monitoring occurrence of a fall of the subject, said system comprising:
   a sensing assembly comprising a first sensing unit configured for placement at the base of the back of the neck of the subject, said first sensing unit comprising a high G 3-axes accelerometer and a low G 3-axes accelerometer; and
   a base configured to wirelessly communicate with said sensing assembly;
   said sensing assembly being configured to wirelessly transmit acceleration data measured by said high G 3-axes accelerometer and acceleration data measured by said low G 3-axes accelerometer to said base, said acceleration data being correlated to the spine of the subject due to said placement at the base of the back of the neck of the subject;
   wherein said base is configured to receive said acceleration data measured by said high G 3-axes accelerometer and acceleration data measured by said low G 3-axes accelerometer sent by said sensing assembly;
   said base being further configured to process the acceleration data measured by said high G 3-axes accelerometer and said acceleration data measured by said low G 3-axes accelerometer;
   said base being further configured to identify a fall of the subject based at least on said acceleration data measured by said high G 3-axes accelerometer and correlated to the spine of the subject due to said placement at the base of the back of the neck of the subject;
   wherein said base is further configured to analyse said acceleration data measured by said high G 3-axes accelerometer and by said low G 3-axes accelerometer and correlated to the spine of the subject due to said placement at the base of the back of the neck of the subject to monitor the activity of the subject associated with displacement amplitude of the trunk of the subject ranging from low to high and to monitor occurrence of a fall.

3. The system according to claim 2, wherein said base is further configured to compare an acceleration of the subject as measured by said low G 3-axes accelerometer with a predetermined acceleration of the subject at rest, thereby yielding an energy level of the subject.

4. The system according to claim 2, wherein
said first sensing unit further comprises a gyroscope;
said sensing assembly is further configured to wirelessly transmit data measured by said gyroscope;
said base is further configured to receive data measured by said gyroscope; and
said base is further configured to determine velocity of lateral movements and back and forth movements of the trunk of the subject from said data measured by said gyroscope.

5. The system according to claim 4,
wherein said base further comprises an analog-to-digital converter configured to digitize data received from said sensing assembly;
said base further comprises a memory having the capability to store said data digitized by said analog-to-digital converter; and
said base is further configured to process said digitized data stored in said memory.

6. The system according to claim 2, wherein said base is further configured to compare the acceleration of the subject as measured by said high G 3-axes accelerometer and by said low G 3-axes accelerometer with the acceleration at rest of the subject over periods of time of 1 minute, of 5 minutes, of 30 minutes or over longer periods of time.

7. The system according to claim 2,
wherein said base is configured to determine, from said data measured by said high G 3-axes accelerometer, an amplitude of an impact if the subject experiences an impact; and
said base is further configured to compare said amplitude of impact to a predetermined impact threshold and to identify a fall of said subject and a corresponding severity of the fall as a result of said comparison.

8. The system according to claim 2, wherein said base is further configured for automatically detecting abnormal variations in the subject's accelerations as measured by said sensing assembly and for emitting a request for intervention or an alarm upon detecting said abnormal variations.

9. The system according to claim 8, wherein the base is further configured to detect said abnormal variations of the subject's activity as at least one of: immobility, interruption of breathing movements, and hyperactivity of a predetermined critical level different from a normal state of said subject.

10. The system according to claim 2, further comprising at least one additional detector, said at least one additional detector comprising at least one of: three-dimensional locators, interphones, motion sensors, presence detectors, pillbox sensors, smoke detectors and household appliance detectors, said base being further configured to be in wireless communication with said at least one additional detector.

11. The system according to claim 2, wherein said base is further configured to assess, from acceleration data received from said sensing assembly, the dynamics of the trunk of the subject and to assess the activity of the subject as critical or normal based on thresholds predetermined for the subject.

12. The system according to claim 2, said sensing assembly further comprising one of a RFID, ultrasound or camera unit configured to measure the height of the subject along a vertical axis;
wherein said base is further configured to use the measured height of the subject along the vertical direction to differentiate between actual fall events and false alarms.

13. The system according to claim 7, wherein said base is configured to use impact waves to differentiate between actual fall events and non-fall events.

14. The system according to claim 2,
wherein the sensing assembly further comprises a second sensing unit configured to be located at a wrist of the subject, said sensing assembly being configured to send data measured by said first and second sensing units to said base;
wherein said first sensing unit and said second sensing unit are configured for connection via a wireless communication link;
said base being configured to receive data from said first and second sensing units and for analyzing said data measured by said first sensing unit and said data measured by said second sensing unit to determine activity levels of the subject.

15. The system according to claim 14, wherein said base is configured to perform an analysis of data measured by said first sensing unit and of data measured by said second sensing unit, and to determine, as a result of said analysis, a precise position of the subject in the subject's environment and to reduce false alarm occurrence based on predetermined thresholds for the subject in the subject's environment.

16. The system according to claim 2,
wherein said sensing assembly further comprises a detector configured for sensing wearing of the sensing assembly by the subject, said sensing assembly being further configured for sending data measured by said detector to said base;
said base being further configured to receive data measured by said detector and for differentiating between a fall of said subject and a fall of the sensing assembly independently of said subject based on said acceleration data measured by said high G 3-axis accelerometer and said data measured by said detector.

17. The system according to claim 2, wherein said base is further configured to be in wireless communication with a server; said base being further configured to transfer said acceleration data measured by said high G 3-axes accelerometer and said acceleration data measured by said low G 3-axes accelerometer to said server and/or to send an alarm.

18. The system according to claim 2, wherein said base and said sensing assembly are further configured for bi-directional voice communication.

19. The system according to claim 2, wherein said sensing assembly is further configured to communicate with said base via a RF frequency.

20. The system according to claim 2, wherein said sensing assembly and/or said base further comprises a help button.

21. A system for monitoring a subject, said system comprising:
a sensing assembly comprising a first sensing unit configured for placement at the base of the back of the neck of the subject;
said first sensing unit comprising a high frequency-low accuracy accelerometer and a low frequency-high accuracy accelerometer; and a base configured to wirelessly communicate with said sensing assembly;

said sensing assembly being configured to wirelessly transmit acceleration data correlated to the spine of the subject due to said placement at the base of the neck of the subject and measured by said accelerometers to said base;

wherein said base is configured to receive said acceleration data measured by said accelerometers and sent by said sensing assembly;

said base being further configured for processing the acceleration data received from said sensing assembly;

said base being further configured to identify body posture and movements of the subject from said acceleration data correlated to the spine of the subject.

22. A system for monitoring a subject, said system comprising:

a sensing assembly comprising a first sensing unit and a second sensing unit;

said first sensing unit comprising a high frequency-low accuracy accelerometer and a low frequency-high accuracy accelerometer and being configured for placement at the base of the back of the neck of the subject; and said second sensing unit comprising an accelerometer and being configured for placement at a wrist of the subject;

said first and second sensing units being configured to wirelessly transmit acceleration data measured by said accelerometers; and a base configured to wirelessly communicate with said first and second sensing units;

wherein said base is configured to receive said acceleration data measured by said accelerometers of said first sensing unit and correlated to the spine of the subject due to said placement at the base of the back of the neck of the subject and sent by said first sensing unit, and said acceleration data measured by said accelerometer of said second sensing unit and sent by said second sensing unit;

said base being further configured to process the acceleration data correlated to the spine of the subject received from said first sensing unit and data received from said second sensing unit;

said base being further configured to track dynamics of the trunk of the subject and to distinguish a fall of the subject from a non-fall impact based at least on said acceleration data.

* * * * *